United States Patent [19]

Patchett et al.

[11] Patent Number: 4,483,850
[45] Date of Patent: Nov. 20, 1984

[54] N-TERMINAL SUBSTITUTED OLIGOPEPTIDE CONVERTING ENZYME INHIBITORS

[75] Inventors: Arthur A. Patchett, Westfield; William V. Ruyle, Scotch Plains, both of N.J.

[73] Assignee: Merck & Co., Inc., Rahway, N.J.

[21] Appl. No.: 466,621

[22] Filed: Feb. 18, 1983

[63] Continuation-in-part of Ser. No. 376,363, May 10, 1982.

[51] Int. Cl.[3] .................. A61K 37/00; A01N 57/00; A01N 43/42; A01N 43/36; C07C 103/52
[52] U.S. Cl. ........................... 424/177; 424/200; 424/258; 424/274; 260/112.5 K
[58] Field of Search .............. 260/112.5 R; 424/177, 424/258, 200, 274

[56] References Cited

U.S. PATENT DOCUMENTS

| | | | |
|---|---|---|---|
| 4,052,511 | 10/1977 | Cushman et al. | 260/112.5 R |
| 4,129,571 | 12/1978 | Ondetti et al. | 260/112.5 R |
| 4,154,960 | 5/1979 | Ondetti et al. | 260/112.5 R |
| 4,303,583 | 12/1981 | Kim et al. | 424/200 |
| 4,344,949 | 8/1982 | Hoefle et al. | 424/258 |
| 4,350,704 | 9/1982 | Hoefle et al. | 424/274 |
| 4,385,180 | 5/1983 | Kim et al. | 424/274 |

FOREIGN PATENT DOCUMENTS

| | | | |
|---|---|---|---|
| 0012401 | 6/1980 | European Pat. Off. | 260/112.5 R |
| 0050800 | 5/1982 | European Pat. Off. | 260/112.5 R |
| 2491469 | 9/1982 | France | |

OTHER PUBLICATIONS

D. W. Cushman, et al., Biochemistry, 16, 5484, (1977).
Y. Piquilloud, et al., Biochem. Biophys. Acta, 206, 136 (1970).
Weeks, et al., Proc. Soc. Exp. Biol. Med., 104, 636, (1969).
Koletsky, et al., Proc. Soc. Exp. Biol. Med., 125, 96, (1967).

Primary Examiner—Delbert R. Phillips
Attorney, Agent, or Firm—Salvatore C. Mitri; Mario A. Monaco

[57] ABSTRACT

N-Terminal substituted oligopeptides are disclosed. The compounds are angiotensin converting enzyme inhibitors useful as antihypertensives.

10 Claims, No Drawings

N-TERMINAL SUBSTITUTED OLIGOPEPTIDE CONVERTING ENZYME INHIBITORS

BACKGROUND OF THE INVENTION

This application is a continuation-in-part of application Ser. No. 376,363 filed May 10, 1982.

This invention is concerned with oligopeptides having angiotensin converting enzyme inhibitor activity.

U.S. Pat. Nos. 4,129,571 and 4,154,960 disclose non-peptide, substituted acyl derivatives of amino acids which are useful as angiotensin converting enzyme inhibitors. More specifically, these compounds are mercapto substituted acyl amino acids and derivatives thereof including the clinically effective antihypertensive compound, captopril, i.e., D-3-mercapto-2-methyl-propanoyl-L-proline. These compound contain an essential sulfhydryl substituent or derivative thereof whereas those of the present invention do not.

European Patent Application No. 0012401 discloses dipeptide enzyme inhibitors of the formula

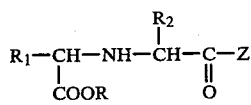

wherein the Z group includes the heterocycle proline.

U.S. Pat. No. 4,052,511 discloses N-carboxyalkanylamino acids which are useful as angiotensin converting enzyme inhibitors.

Oligopeptides where Z in formula A is a di-or tripeptide have been discovered.

DETAILED DESCRIPTION OF THE INVENTION:

An embodiment of the present invention is a compound having the formula

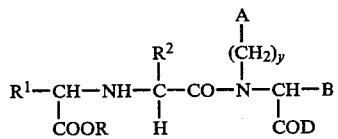

wherein:

R is hydrogen; loweralkyl; aralkyl; or, aryl;

$R^1$ is hydrogen; alkyl of from 1 to 12 carbon atoms which include branched, cyclic and unsaturated alkyl groups; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino; acylamino substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8–12 carbon atoms; aryl or heteroaryl which may be mono-, di-, or trisubstituted by loweralkyl, hydroxy, loweralkoxy, halo, amino, acylamino, lower alkylthio or aminoloweralkyl; benzofused cycloalkyl or bicycloalkyl of from 8 to 12 carbon atoms; arloweralkyl, arloweralkenyl, heteroloweralkyl and heteroloweralkenyl in which the aryl or heteroaryl rings may be mono-, di-, or trisubstituted by halo, lower alkyl, hydroxy, loweralkoxy, amino, lower alkylamino, diloweralkylamino, aminolower alkyl, acylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n$—Q—$(CH_2)_m$ wherein n is 0-2, m is 1-3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, or $SO_2$, N—$R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl;

$R_2$ is lower alkyl, lower alkenyl, or lower alkynyl; substituted lower alkyl, lower alkenyl or lower alkynyl in which the substituent(s) may be lower cyclo alkyl, halo, hydroxy, amino, amidino, acylamino, carboxylower alkyl amino, carbamoyllower alkylamino, hydroxy lower alkylamino, arylamino arlower alkyl amino or heteroarlower alkylamino; substituted lower alkyloxy alkyl, loweralkyl thio alkyl, and lower alkylaminoalkyl wherein the substituent(s) may be the same as those recited above; arlower alkyl and hetero arlower alkyl which may be substituted by lower alkyl, lower alkyloxy, amino, hydroxy halo or acylamino;

in the group

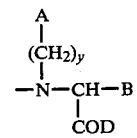

Y is 0 to 4

A is (a) alkyl, including branched unsaturated and cyclic alkyl of 3 to 8 carbon atoms;

(b) benzofused cycloalkyl or bicycloalkyl of 8 to 12 carbon atoms;

(c) aryl or heteroaryl groups which may be mono-, di-, or trisubstituted by loweralkyl, loweralkoxy, halo, amino, acylamino, hydroxy, acyl or acyloxy, and corresponding groups in which the aryl or heteroaryl groups are partially or completely hydrogenated;

(d) lower alkyl including branched and unsaturated groups which may be substituted by aryl or heteroaryl groups and corresponding groups in which the aryl or heteroaryl rings are partially or completely hydrogenated;

B is hydrogen or loweralkyl or

A and B may be joined, together with the carbon atoms to which they are attached to form a ring having the formulae:

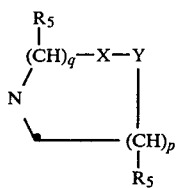 (1)

wherein X and Y taken together are

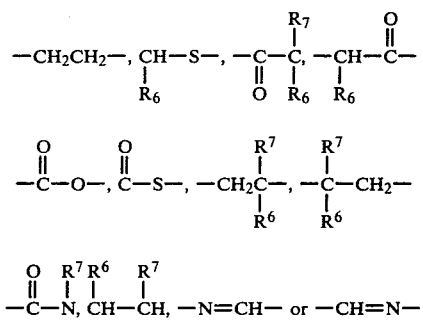

wherein:

R$^5$ and R$^6$ individually are hydrogen; lower alkyl; cycloalkyl; aryl; aralkyl; heteroaryl; lower alkyloxy, lower alkylthio; aryloxy; arylthio; arloweralkyloxy; arlower alkylthio; hydroxy; acyloxy; acyllower alkyl; halo; amino; mono- or disubstituted lower alkyl amino; arlower alkylamino; heteroloweralkylamino; acylamino in which the acyl group may be lower alkanoyl, aroyl, heteroaroyl or heterolower alkanoyl; carbamoyl; or N-substituted carbamoyloxy; and wherein any of these groups containing an aromatic ring, said ring may be mono-, di-, or trisubstituted by lower alkyl, lower alkoxy, loweralkylthio, halo, hydroxy, aryl, aryloxy, arylthio or aralkyl; and wherein any of said groups containing an aryl or heteroaryl group in which said groups are partially or completely hydrogenated;

R$^7$ is hydrogen, loweralkyl, aryl, cycloalkyl, or substituted aryl wherein the substituent can be halo, hydroxy, alkoxy, amino or loweralkyl; or R$^6$ and R$^7$ taken together may be oxo, or, together with the atoms to which they are attached form a 3 to 6 membered ring which may contain 0, 1, or 2 atoms of N, S, or O;

p and q are independently 0 to 3;

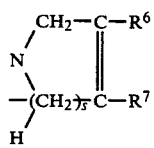 (2)

wherein R$^6$ and R$^7$ are as defined above and s is 0, 1, and 2;

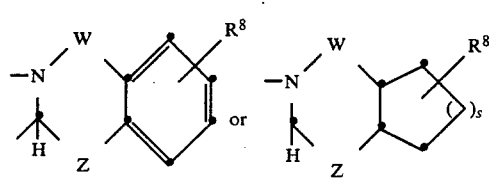 (3)

wherein
W is absent;

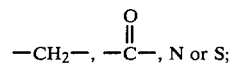, N or S;

Z is —(CH$_2$)$_t$—, where t is 0 to 2, provided that t may not be O when W is absent; —O—; —N—, or —S—;

R$^8$ is hydrogen; lower alkyl; loweralkoxy; hydroxy; halo, lower alkylthio; amino; acylamino; or cyano;

P is 1 to 3;

D is an amino acid or amino acid derivative, R$_9$—R$_{11}$, or a dipeptide R$_9$—R$_{10}$—R$_{11}$ wherein R$_9$ and R$_{10}$ are independently selected from alanine, leucine, isoleucine, lysine, arginine, glycine, histidine, methionine, ornithine, phenylalanine, serine, threonine, tryptophane, tyrosine or valine, R$_{11}$ is OH, NH$_2$ or OR$_{12}$ wherein R$_{12}$ is lower alkyl, aryl or aralkyl; and, the pharmaceutically acceptable salts thereof.

Pharmaceutically acceptable salts are salts of the formula I compounds with various inorganic and organic acids and bases. Such salts include ammonium salts, alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like; also salts with organic or inorganic acids such as HCl, HBr, H$_2$SO$_4$, H$_3$PO$_4$, methanesulfonic acid, toluenesulfonic acid, maleic acid, oxalic acid, fumaric acid, camphorsulfonic acid, acetic acid, pamoic acid, isethionic acid, pivalic acid and the like. The non-toxic physiologically acceptable salts are preferred, although other salts are also useful, e.g., in isolating or purifying the product.

The salts may be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The alkyl substituents recited above denote straight and branched chain hydrocarbons of C$_1$ to C$_{12}$ such as methyl, hexyl, propyl, docecyl isopentyl, isopropyl, neopentyl etc.

Loweralkyl denotes alkyl groups of C$_1$ to C$_8$ such as ethyl, isobutyl, 4-methylpentyl, and the like.

Alkenyl and alkynyl denote alkyl groups as described above which are modified so that each contains a carbon carbon double bond or triple bond, respectively, such as vinyl, 2-butenyl and 1-hexynyl.

Cycloalkyl denotes rings composed of 5 to 8 methylene groups, each of which may be substituted or unsubstituted with other hydrocarbon substituents, such as, for example, cyclopentyl, cycloheptyl, 4-methyl cyclohexyl and the like.

Benzofused cycloalkyl groups denote a cycloalkyl ring of 5 to 8 carbon atoms to which is fused a benzene ring such as indanyl or tetralyl groups.

Bicycloalkyl denotes two cycloalkyl rings of 5 to 8 carbon atoms each joined together in any allowable way such as perhydroindane, octahydronaphthalene, bicyclo 3:1:3 octane and spiro 4:0:4 nonane.

The loweralkoxy substituent represents a loweralkyl group as described above attached through an oxygen bridge.

The aralkyl and heteroaralkyl substituents recited above represent aryl or heteroaryl groups as herein defined attached through a straight or branched chain hydrocarbon of from one to six carbon atoms, for example, benzyl, phenethyl, 3,3-diphenylpropyl, 3-indolylmethyl, and the like.

Halo means chloro, bromo, iodo, or fluoro.

The aryl substituent represents phenyl, naphthyl, or biphenyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl; as well as any bicyclic group in which any of the above heterocyclic rings is fused to another aromatic ring, such as, for example, indolyl, quinolinyl, isoquinolinyl, benzimidazolyl, benzothiazolyl, benzthienyl, and naphthyridyl.

The acylamino substituent represents loweralkanoylamino and aroylamino.

Of the various heterocyclic elements generally defined above as

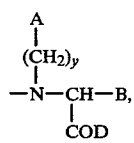

the following are specifically included and are preferred:

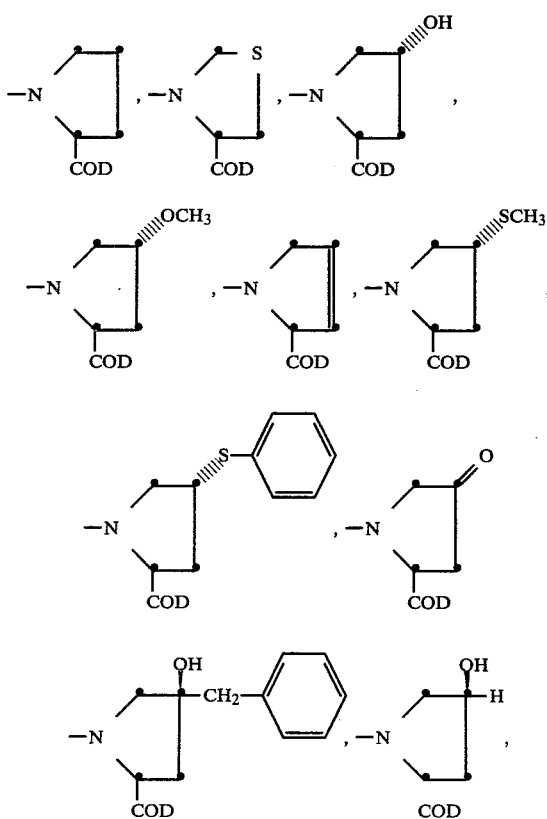

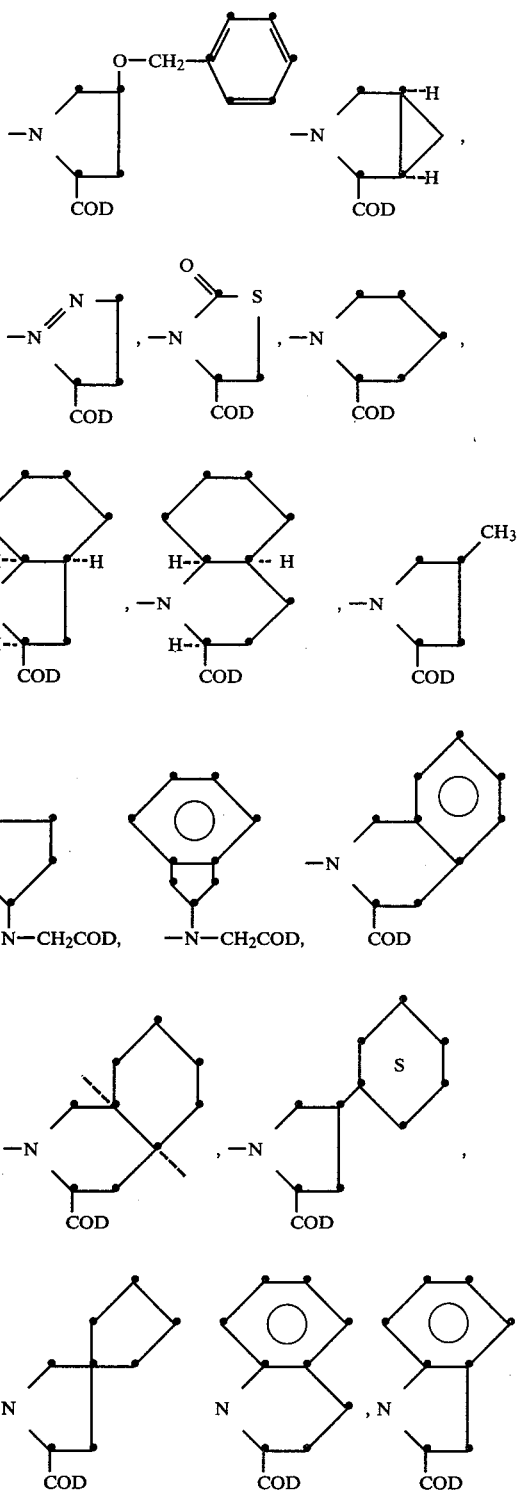

The Formula I compounds can be used in the form of salts derived from inorganic or organic acids. Included among such salts are the following: acetate, adipate, alginate, aspartate, benzoate, benzenesulfonate, bisulfate, butyrate, and citrate.

the $R_2$ aminoloweralkyl moiety is exemplified by groups such as

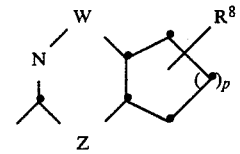

wherein W is O; Z is CH$_2$; p is 2; and, R$^8$ is H;

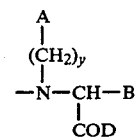

wherein y is O; A is 2-indanyl; B is H; and, D is as defined above.

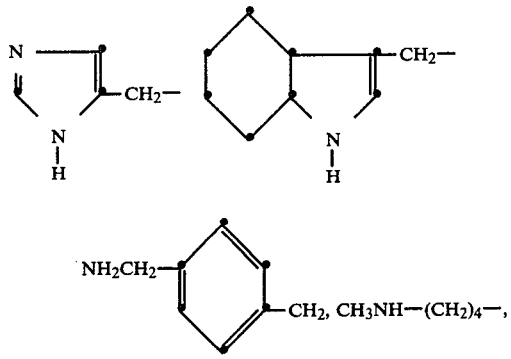

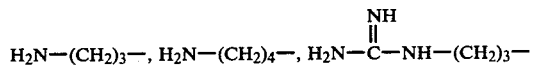

and the like.

Preferred compounds of the present invention are those of Formula I wherein:

R is hydrogen or loweralkyl;

R$^1$ is alkyl of 1-10 carbon atoms which include branched, cyclic and unsaturated alkyl groups; substituted loweralkyl wherein the substituent can be hydroxy, lower alkylthio, amino, alkylamino, lowerdialkylamino, and acylamino; substituted loweralkyl having the formula R$_A^1$(CH$_2$)$_n$—Q—(CH$_2$)$_m$—wherein n is 0-2, m is 1-3, R$_A^1$ is aryl or heteroaryl optionally substituted by alkyl, halo, dihalo, amino, cyano, hydroxy, or alkoxy, and Q is O, S, N-R$^1$, CONR$^1$, NR$^1$CO, or CH=CH wherein R$_B^1$ is hydrogen, loweralkyl, aralkyl, loweralkanoyl, or aroyl and R$_C^1$ is hydrogen or loweralkyl; aralkyl or heteroaralkyl which include branched loweralkyl groups; substituted aralkyl or substituted heteroaralkyl which include branched loweralkyl groups wherein the loweralkyl substituents can be amino, acylamino, or hydroxy and the aryl and heteroaryl substituents can be loweralkyl, halo, dihalo, amino, cyano, hydroxy, loweralkoxy, aminoloweralkyl, or hydroxyloweralkyl.

R$^2$ is —(CH$_2$)$_k$—X—(CH$_2$)$_j$—NH$_2$; wherein k is 1 or 2, j is 1 or 2, and X is CH$_2$, FCH, HOCH, —CH=CH—, —C≡C—, or lower alkyl;

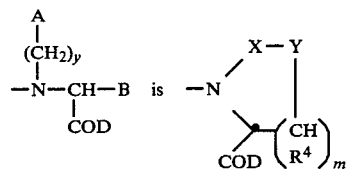

where X and Y taken together are —CH$_2$—CH$_2$—; R$^4$ is hydrogen; m is 1; and D is as defined above;

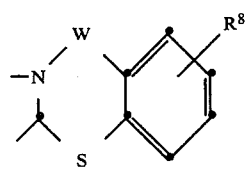

wherein W and Z are CH$_2$; and, R$^8$ is H;

The compounds of Formula I inhibit angiotensin converting enzyme and thus block conversion of the decapeptide angiotensin I to angiotensin II. Angiotensin II is a potent pressor substance. Thus blood-pressure lowering can result from inhibition of its biosynthesis especially in animals and humans whose hypertension is angiotensin II related. Furthermore, converting anzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta,* 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.,* 104 646 (1960) or in a high renin rat model such as that of S. Koletsky et al., *Proc. Soc. Exp. Biol. Med.,* 125, 96 (1967).

Thus, the compounds of the invention are useful in treating hypertension. They are also of value in the management of acute and chronic congestive heart failure, in the treatment of secondary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

In the management of hypertension and those clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics. For example, the compounds of this invention can be given in combination with such compounds as amiloride, atenolol, benzofluoromethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, hydroflumethiazide, metolazone, metoproloItartate, methylclothiazide, methyldopa, methyldopate hydrochloride, minoxidil, pargyline hydrochloride, polythiazide, prazosin, propranolol, *rauwolfia serpentina,* rescinnamine, reserpine, sodium nitroprusside, spironolactone, timolol, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 2.5–250 milligrams per day range can be effectively combined at levels at the 0.5–250 milligrams per day range with the following compounds at the indicated per day dose range: hydrochlorothiazide (5–200 mg), chlorothiazide (125–2000 mg), ethacrynic acid (15–200 mg), amiloride (5–20 mg), furosemide (5–80 mg), propranolol (20–480 mg), timolol (5–60 mg.) and methyldopa (65–2000 mg). In addition, triple drug combinations of hydrochlorothiazide (15–200 mg) plus amiloride (5–20 mg) plus converting enzyme inhibitor of this invention (3–200 mg) or hydrochlorothiazide (15–200 mg) plus timolol (5–60) plus the converting enzyme inhibitor of this invention (0.5–250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The compounds of Formula I may be prepared by using any convenient process.

The following equations illustrate one such process.

Step 1:

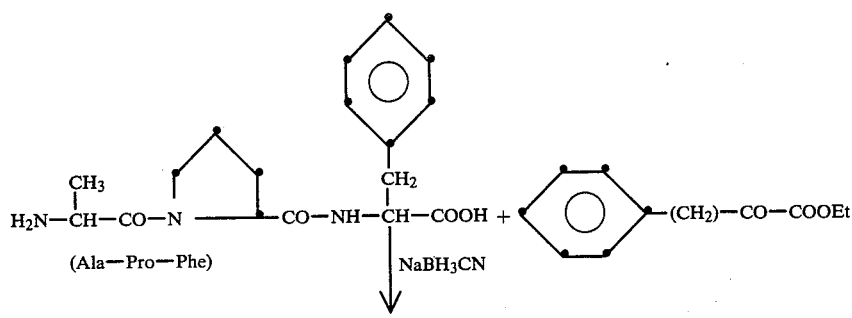

Step 2:

-continued

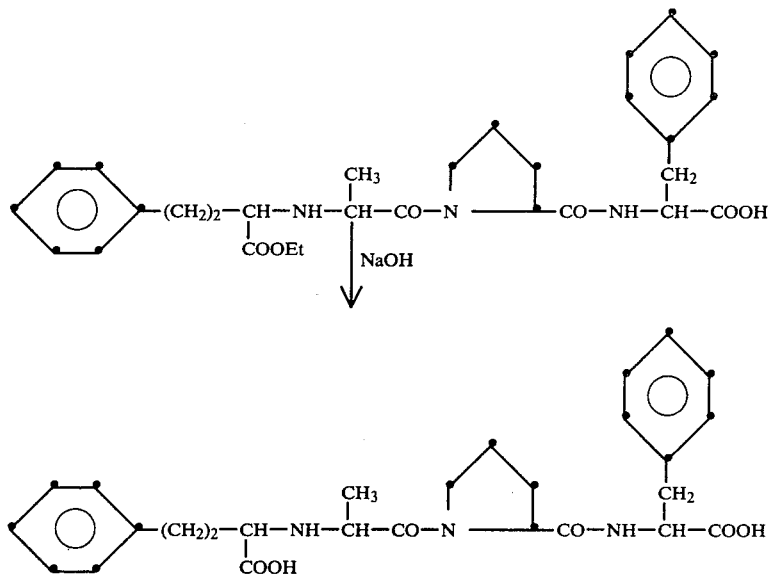

The Step 1 reduction is ordinarily carried out in a liquid reaction medium such as an alkanol e.g. ethanol. Other reducing agent systems can be used e.g. Raney nickel /H₂, Group VIII metal complex catalyst/H₂ and the like. In cases where the tripeptide contains a reactive group(s) in addition to the α-amino groups, e.g. Lys-Pro-Phe, it is necessary to use a "blocked" derivative e.g. N -Boc-Lys-Pro-Phe in the reaction with keto ester and sodium cyanoborohydride.

Step II is a conventional alkaline hydrolysis and other conventional base systems may be used.

In compounds of general Formula I, the carbon atoms to which $R_1$ and $R_2$ are attached may be asymmetric. The compounds accordingly exist in diastereoisomeric forms or in mixtures thereof.

If desired, the diastereomeric products can be separated by conventional chromatographic or fractional crystallization methods. Although, the amino acid part-structures, i.e.,

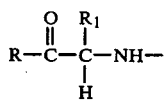

and

of Formula I are generally preferred in the L- or S-configuration, diastereomers containing D-amino acids have activity dependent upon their structures and have advantages in respect to metabolic stability in vivo and therefore can be utilized in mixture or as pure diastereomeric compounds.

The following examples illustrate preparation of representative compounds of the present invention.

EXAMPLE 1

N-(1-Ethoxycarbonyl-3-phenylpropyl)-L-alanyl-L-prolyl-L-phenylalanine

To a solution of 333 mg, (1.0 millimole) of L-alanyl-L-prolyl-L-phenylalanine and 1.03 g (5.0 millimole) of ethyl 2-keto-4-phenylbutyrate in 5 ml of ethanol was added 3 g of powdered molecular sieves, (activated type 4A). The resulting suspension was stirred at room temperature under nitrogen while a solution of 125 mg (2 millimole) of sodium cyanoborohydride in 2 ml of ethanol was added during six hours. After stirring overnight at room temperature, the mixture was filtered, and the filtrate concentrated in vacuo. The residual material was taken up in 75 ml of water and 40 ml of Dowex 50 H⁺ resin was added. The mixture was extracted with three 50 ml portions of ethyl acetate. The aqueous phase and resin were placed on top of a column of 60 ml of Dowex 50 H⁺ resin, and the column was then washed with water until the eluate was only faintly acid (pH ca. 6). The column was then eluted with a 3% pyridine solution in water. The fractions containing the desired product were combined and concentrated, and the product, N-(1-ethoxycarbonyl-1-phenylpropyl)-L-alanyl-L-propyle-L-phenylalanine, was lyophilized from water.

The PMR sprectrum of this product in Me₂SO-d₆ showed: δ 1.08 (d, 3H, J=6 Hz, alanine-CH₃);δ1.2 and 1.3 (t, 3H total, J=3Hz, ethyl-CH₃, 2 diastereomers);δ7.25 (s(broad), 10H, aryl). Other signals, δ1.5-4.6, appearing as unresolved multiplets were consistent with the expected structure. Thin layer chromatography on silica gel, using butanol, acetic acid, water 65/25/10 as eluant showed two spots with Rf 0.38 and 0.48 respectively. Mass spectroscopy using the "Fast Atom Bombardment" (FAB) technique showed a prominent M+1 peak at 524 mass units.

In a similar manner, other tripeptides, such as L-alanyl-L-prolyl-L-leucine and the like may be treated with ethyl-2-keto-4-phenylbutyrate and sodium cyanoborohydride as in Example 1 to yield the corresponding N-terminally substituted tripeptides, such as N-(1- ethoxycarbonyl-2-phenylpropyl)-L-alanyl-L-prolyl-L-leucine.

Furthermore the same method may be used to prepare N-terminally substituted tetrapeptides, for example, N-(1-ethoxycarbonyl-2-phenylpropyl)-L-alanyl-L-prolyl-L-histidyl-L-leucine by treatment of L-alanyl-L-prolyl-L-histidyl-L-leucine with the keto ester and sodium cyanoborohydride as in Example 1.

EXAMPLE 2

N-(1-Carboxy-3-phenylpropyl)-L-alanyl-L-prolyl-L-phenylalanine

A solution of 1.0 millimole of N-(1-Ethoxycarbonyl-3-phenylpropyl)-L-alanyl-L-prolyl-L-phenylalanine in 4 ml of 1N NaOH was kept at room temperature for 18 hours. The solution was put on a column of 300 ml of Dowex 50 (H+) resin. After washing with 500 ml water, the product was eluted with 3% aqueous pyridine solution. After concentration of the eluate in vacuo and lyophilization, the N-(1-carboxy-3-phenylpropyl)-L-alanyl-L-prolyl-L-phenylalanine product was obtained as an amorphous solid.

Thin layer chromatography and HPLC of this product showed the presence of two substances as expected for a mixture of diastereomers. Mass spectroscopy by the FAB technique showed a prominent M+1 peak at 496 mass units.

Other, similarly substituted tripeptide and tetrapeptide esters may be saponified to yield di-acids as in Example 2.

Exemplary of the various keto acids and keto esters which can be used in the processes described above are those listed in Table I below:

TABLE I
Keto Acids and Esters of the Formula R'COCOOR (a) 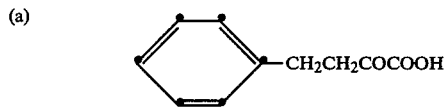

(b) 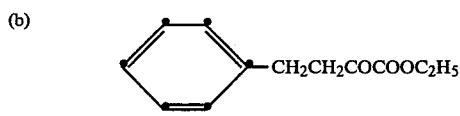

(c) 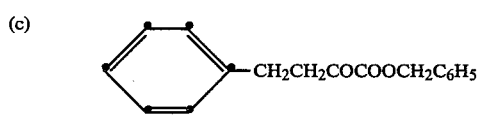

(d) 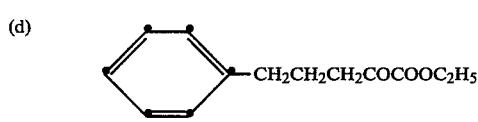

(e) 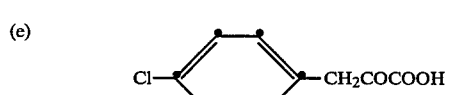

TABLE I-continued
Keto Acids and Esters of the Formula R'COCOOR (f) 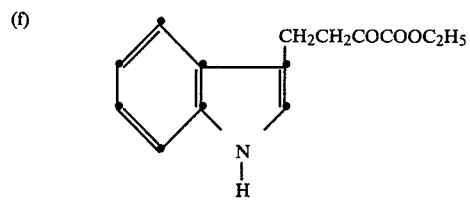

(g) 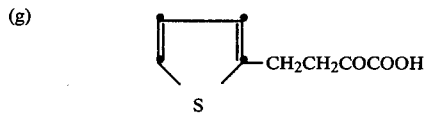

(h) 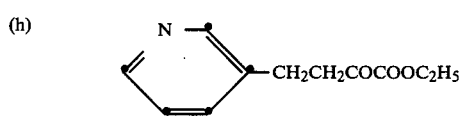

(i) 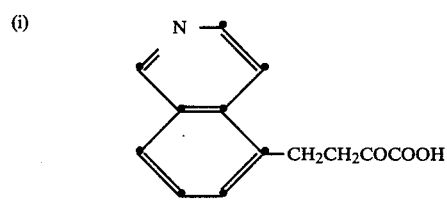

(j) 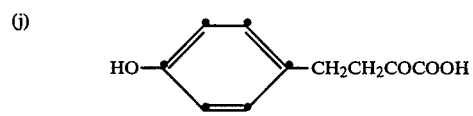

(k) 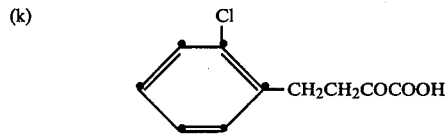

(l) 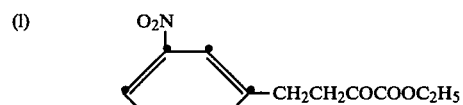

(precursor for the corresponding amino compound)

(m) 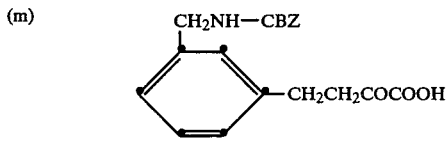

(precursor for the corresponding amino compound)

Other compounds of Formula I which can be prepared using an available process or a process analogous to those in Examples 1 or 2 are exemplified, but not limited to, those set forth in Table II below wherein X' represents F and Cl.

TABLE II
Illustrative Compounds of Formula I

TABLE II-continued
Illustrative Compounds of Formula I
(A)
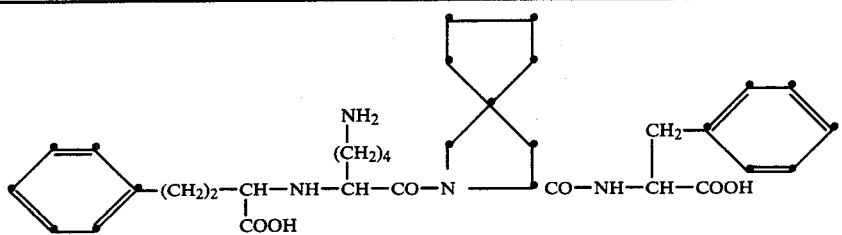
(B)
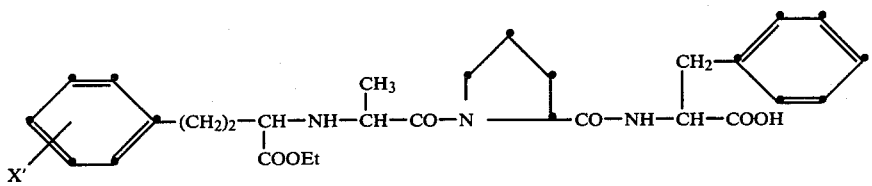
(C)
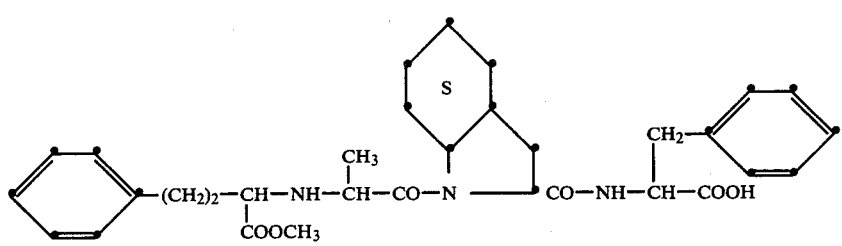
(D)
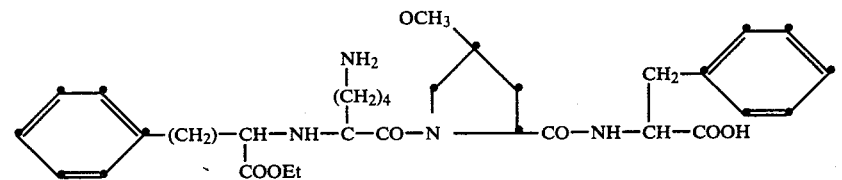
(E)
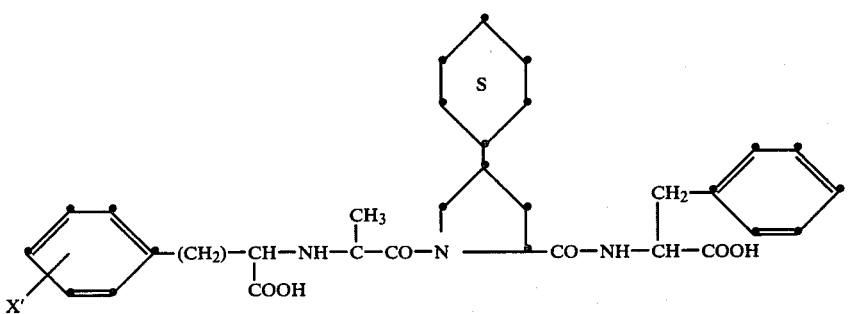
(F)
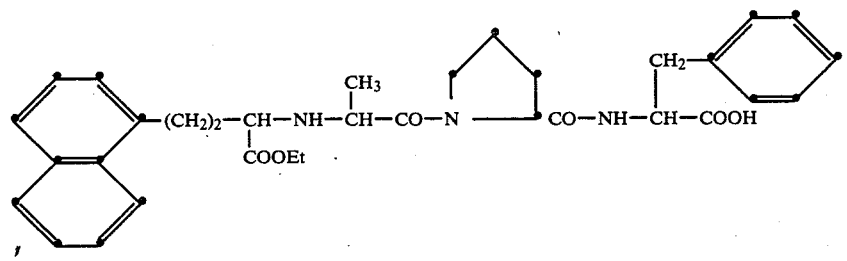
(G)
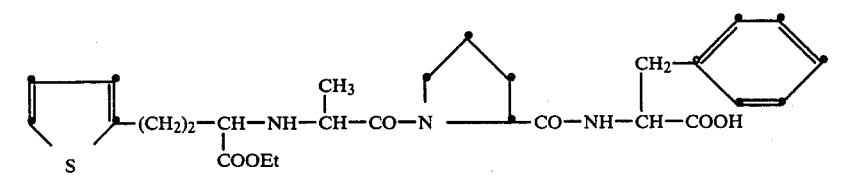

TABLE II-continued
Illustrative Compounds of Formula I (H) 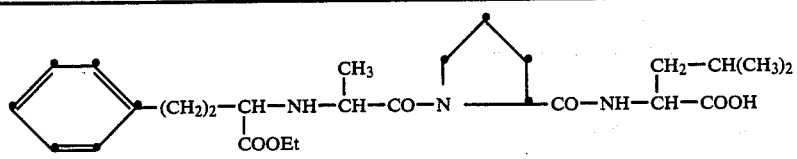

(I) 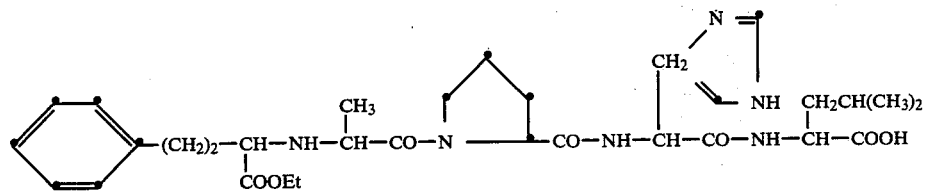

(J) 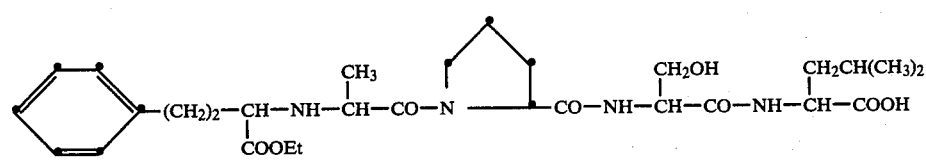

(K) 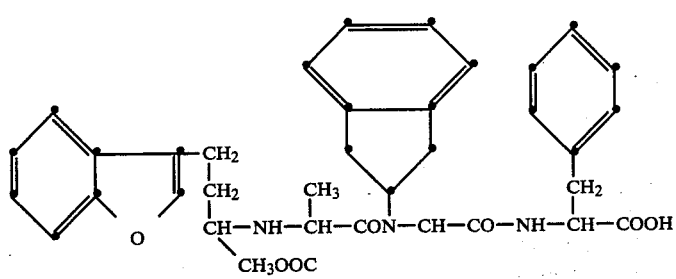

(L) 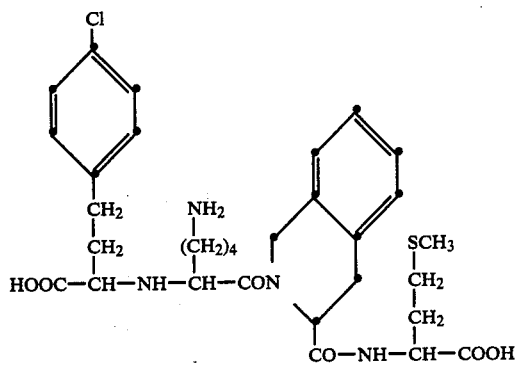

What is claimed is:

1. Compounds having the formula:

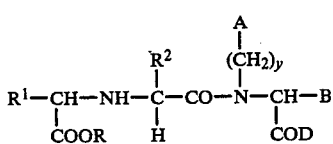
(I.)

wherein:

R is hydrogen; loweralkyl; aralkyl; or, aryl;

R¹ is hydrogen; alkyl of from 1 to 12 carbon atoms which include branched, cyclic and unsaturated alkyl groups; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino; acylamino substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8-12 carbon atoms; aryl or heteroaryl which may be mono-, di-, or trisubstituted by loweralkyl, hydroxy, loweralkoxy, halo, amino, acylamino, lower alkylthio or aminoloweralkyl; benzofused cycloalkyl or bicycloalkyl of from 8 to 12 carbon atoms; arloweralkyl, arloweralkenyl, heteroloweralkyl and heteroloweralkenyl in which the aryl or heteroaryl rings may be mono-, di-, or trisubstituted by halo, lower alkyl, hydroxy, loweralkoxy, amino, lower alkylamino, diloweralkylamino, aminolower alkyl, acylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n—Q—(CH_2)_m$ wherein n is 0-2, m is 1-3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, or $SO_2$, $N—R_B{}^1$, $CONR_C{}^1$, $NR_C{}^1CO$, $CH=CH$ wherein $R_B{}^1$ is hydrogen, loweralkyl, aryl, aralkyl, loweralkanoyl, or aroyl, and $R_C{}^1$ is hydrogen, or loweralkyl;

$R_2$ is lower alkyl, lower alkenyl, or lower alkynyl; substituted lower alkyl, lower alkenyl or lower alkynyl in which the substituent(s) may be lower cyclo alkyl, halo, hydroxy, amino, amidino, acylamino, carboxylower alkyl amino, carbamoyllower alkylamino, hydroxy lower alkylamino, arylamino arlower alkyl amino or heteroarlower alkylamino; substituted lower alkyloxy alkyl, loweralkyl thio alkyl, and lower alkylaminoalkyl wherein the substituent(s) may be the same as those recited above; arlower alkyl and heteroarlower alkyl which may be substituted by lower alkyl, lower alkyloxy, amino, hydroxy halo or acylamino;

in the group

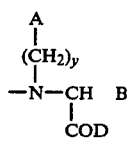

y is 0 to 4
A is
(a) alkyl, including branched unsaturated and cyclic alkyl of 3 to 8 carbon atoms;
(b) benzofused cycloalkyl or bicycloalkyl of 8 to 12 carbon atoms;
(c) aryl or heteroaryl groups which may be mono-, di-, or trisubstituted by loweralkyl, loweralkoxy, halo, amino, acylamino, hydroxy, acyl or acyloxy, and corresponding groups in which the aryl or heteroaryl groups are partially or completely hydrogenated;
(d) lower alkyl including branched and unsaturated groups which may be substituted by aryl or heteroaryl groups and corresponding groups in which the aryl or heteroaryl rings are partially or completely hydrogenated;
B is hydrogen or loweralkyl or
A and B may be joined, together with the carbon atoms to which they are attached to form a ring having the formulae:

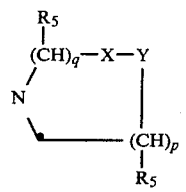

wherein X and Y taken together are

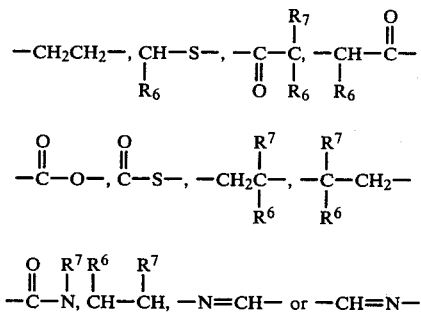

wherein:
$R^5$ and $R^6$ individually are hydrogen; lower alkyl; cycloalkyl; aryl; aralkyl; heteroaryl; lower alkyloxy, lower alkylthio; aryloxy; arylthio; arloweralkyloxy; arlower alkylthio; hydroxy; acyloxy; acyllower alkyl; halo; amino; mono- or disubstituted lower alkyl amino; arlower alkylamino; heteroloweralkylamino; acylamino in which the acyl group may be lower alkanoyl, aroyl, heteroaroyl or heterolower alkanoyl; carbamoyl; or N-substituted carbamoyloxy; and wherein any of these groups containing an aromatic ring, said ring may be mono-, di-, or trisubstituted by lower alkyl, lower alkoxy, loweralkylthio, halo, hydroxy, aryl, aryloxy, arylthio or aralkyl; and wherein any of said groups containing an aryl or heteroaryl group in which said groups are partially or completely hydrogenated;
$R^7$ is hydrogen, loweralkyl, aryl, cycloalkyl, or substituted aryl wherein the substituent can be halo, hydroxy, alkoxy, amino or loweralkyl; or
$R^6$ and $R^7$ taken together may be oxo, or, together with the atoms to which they are attached form a 3 to 6 membered ring which may contain 0, 1, or 2 atoms of N, S, or O;
p and q are independently 0 to 3;

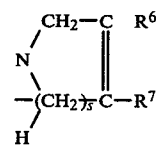

wherein $R^6$ and $R^7$ are as defined above and s is 0, 1, and 2;

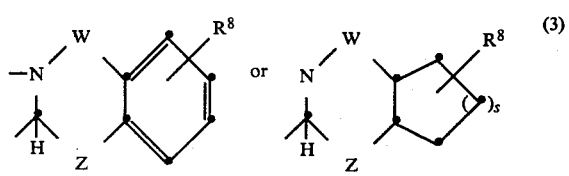

wherein

W is absent; —CH$_2$—, N or S;

Z is —(CH$_2$)$_t$—, where t is 0 to 2, provided that t may not be O when W is absent; —O—; —N—, or —S—;

$R^8$ is hydrogen; lower alkyl; loweralkoxy; hydroxy; halo, lower alkylthio; amino; acylamino; or cyano;

p is 1 to 3;

D is an amino acid or amino acid derivative, R$_9$—R$_{11}$, or a dipeptide R$_9$—R$_{10}$—R$_{11}$ wherein R$_9$ and R$_{10}$ are independently selected from alanine, leucine, isoleucine, lysine, arginine, glycine, histidine, methionine, ornithine, phenylalanine, serine, threonine, tryptophane, tyrosine, or valine, R$_{11}$ is OH, NH$_2$ or OR$_{12}$ wherein R$_{12}$ is loweralkyl, aryl, or aralkyl; and, the pharmaceutically acceptable salts thereof.

2. Compounds of claim 1 wherein R$_1$ is Het(CH$_2$)$_n$ and R is H or lower alkyl.

3. Compounds of claim 1 wherein R$_1$ is Ar(CH$_2$)$_n$ and R is H or lower alkyl.

4. Compounds of claim 3 wherein R$_1$ is

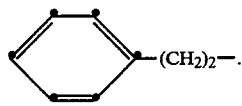

5. Compounds of claim 4 wherein R$_2$ is CH$_3$ or (CH$_2$)$_4$—NH$_2$.

6. Compounds of claim 5 wherein D is R$_9$—R$_{11}$ or R$_9$—R$_{10}$—R$_{11}$.

7. Compounds of claim 5 wherein D is

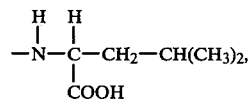

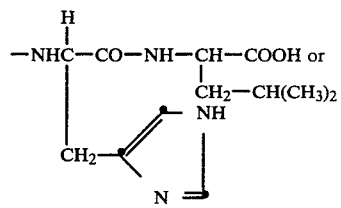

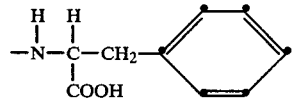

8. Compounds of claim 6 wherein R is H or C$_2$H$_5$.

9. A pharmaceutical composition useful for treating hypertension which comprises a pharmaceutically acceptable carrier; and, an antihypertensively effective amount of a compound of claim 1.

10. A method for treating hypertension which comprises administering to a patient in need of such treatment an antihypertensively effective amount of a compound of claim 1.

* * * * *